(12) United States Patent
De Smet (10) Patent No.: US 8,151,643 B2
(45) Date of Patent: Apr. 10, 2012

(54) DEVICE FOR NON-DESTRUCTIVE TESTING OF A STRUCTURE BY VIBRATORY ANALYSIS

(75) Inventor: Marie-Anne De Smet, Monbrun (FR)

(73) Assignee: Airbus France, Toulouse (FR)

( * ) Notice: Subject to any disclaimer, the term of this patent is extended or adjusted under 35 U.S.C. 154(b) by 534 days.

(21) Appl. No.: 12/301,702

(22) PCT Filed: May 16, 2007

(86) PCT No.: PCT/EP2007/054759
§ 371 (c)(1), (2), (4) Date: Jun. 23, 2009

(87) PCT Pub. No.: WO2007/135057
PCT Pub. Date: Nov. 29, 2007

(65) Prior Publication Data
US 2009/0301197 A1    Dec. 10, 2009

(30) Foreign Application Priority Data
May 24, 2006  (FR) ................................. 06 51903

(51) Int. Cl.
*G01N 29/14* (2006.01)
(52) U.S. Cl. ........................................... 73/587
(58) Field of Classification Search ............... 73/583, 73/587, 602, 801, 802; 702/36, 39
See application file for complete search history.

(56) References Cited

U.S. PATENT DOCUMENTS

| | | | |
|---|---|---|---|
| 3,511,086 A | 5/1970 | Woodmansee | |
| 3,970,074 A | 7/1976 | Mogos et al. | |
| 4,433,637 A | 2/1984 | Buirley et al. | |
| 4,810,881 A | 3/1989 | Berger et al. | |
| 5,047,719 A | 9/1991 | Johnson et al. | |

(Continued)

FOREIGN PATENT DOCUMENTS
DE    4220544 A1    1/1994
(Continued)

OTHER PUBLICATIONS
International Search Report dated Aug. 14, 2007.

*Primary Examiner* — John Chapman, Jr.
(74) *Attorney, Agent, or Firm* — Perman & Green, LLP (57) ABSTRACT

A device for non-destructive testing of a structure likely to contain a defect, including microsensors for measuring vibratory waves emitted by the structure at different points of a surface of the structure, the aforementioned microsensors being integrated in a flexible housing capable of adhering on the surface of the structure to be tested. The disclosed embodiments are applicable to all industrial sectors where testing of the integrity of structures is important, in particular in areonautics.

20 Claims, 4 Drawing Sheets

U.S. PATENT DOCUMENTS

| | | | |
|---|---|---|---|
| 5,166,573 A | 11/1992 | Brown | |
| 5,293,555 A * | 3/1994 | Anthony | 702/36 |
| 5,659,248 A | 8/1997 | Hedengre et al. | |
| 5,911,158 A | 6/1999 | Henderson | |
| 6,077,228 A | 6/2000 | Schonberger | |
| 6,370,964 B1 * | 4/2002 | Chang et al. | 73/862.046 |
| 6,399,939 B1 * | 6/2002 | Sundaresan et al. | 250/231.1 |
| 6,564,640 B1 * | 5/2003 | Allaei | 73/583 |
| 7,209,539 B2 | 4/2007 | De Smet | |
| 7,430,911 B2 * | 10/2008 | Qing et al. | 73/587 |
| 2001/0015643 A1 | 8/2001 | Goldfine et al. | |
| 2003/0031296 A1 | 2/2003 | Hoheisel | |
| 2003/0188579 A1 | 10/2003 | Evans et al. | |
| 2005/0062470 A1 | 3/2005 | Shoji | |

FOREIGN PATENT DOCUMENTS

| | | |
|---|---|---|
| EP | 0245147 A1 | 11/1987 |
| EP | 0577244 A2 | 1/1994 |
| EP | 0672380 A | 9/1995 |
| EP | 0887642 A1 | 12/1998 |
| FR | 2836994 A1 | 9/2003 |
| FR | 1403635 A | 3/2004 |
| FR | 2874430 A | 2/2006 |
| FR | 2874430 A1 | 2/2006 |
| GB | 2222255 A | 2/1990 |

* cited by examiner

DEVICE FOR NON-DESTRUCTIVE TESTING OF A STRUCTURE BY VIBRATORY ANALYSIS

CROSS REFERENCE TO RELATED APPLICATIONS

This application is the National Stage of International Application No. PCT/EP2007/054759 International Filing Date, 16 May 2007, which designated the United States of America, and which International Application was published under PCT Article 21 (2) as WO Publication No. WO2007/135057 and which claims priority from French Application No. 0651903, filed on 24 May 2006, the disclosures of which are incorporated herein by reference in their entireties.

This application is also related to U.S. patent application Ser. No. 12/301,646, filed on Jun. 23, 2009, (International Application Serial No. PCT/EP2007/054762) and U.S. patent application Ser. No. 12,301,701, filed on Jun. 23, 2009, (International Application Serial No. PCT/EP2007/054751) the disclosures of which are incorporated herein by reference in their entireties.

BACKGROUND

1. Field

The disclosed embodiments concern a device for non-destructive testing of a structure by vibratory analysis, containing means to measure the vibratory waves emitted by the structure so as to identify abnormal vibrations caused by a defect in the structure. The means of measuring are incorporated into a flexible housing capable of adhering to the surface of the structure to be tested. The disclosed embodiments have applications in the non-destructive testing (NDT) of aircraft structures, but may be used in any industrial sector where testing the integrity of workpieces is important, such as the automotive, railroad, naval-construction, or nuclear sectors.

2. Brief Description of Related Developments

In the operation and maintenance of aircraft, it is necessary to employ testing methods that can determine whether the structures have been damaged by cracks or fissures, without harming the parts constituting the structure. The techniques used are jointly referred to as "non-destructive testing" (NDT). NDT techniques are numerous and constantly changing, because the industrial sectors concerned have a need for improved performance from these NDT techniques. The air-transport and civil-engineering sectors are always on the lookout for ever more effective NDT techniques to meet the dual requirements of safety and their desire for cost-reduction.

Accordingly, the disclosed embodiments are designed specifically to detect abnormal vibrations in aircraft structures while the aircraft is in flight. In some cases these vibrations are indicators of the appearance of defects in the structures, e.g., the development of fissures or cracks in the material constituting the aircraft's structure.

For example, there are means of testing by using x-ray radiography or magnetic induction that can detect defects in a structure, but these means are difficult to apply, and unsuitable for use on an aircraft structure unless the aircraft is stationary.

There are also visual testing means for detecting the appearance of fissures, but in general the structures in which defects are most likely to develop are structures that present access difficulties, such as fastenings or complex moving structures. These means enable the detection of fissures only when the fissures emerge on a surface directly accessible to the operator, thus visual testing means do not provide for effective predictive maintenance of the structures.

All of these means of testing require that the aircraft be immobilized on the ground for the conduct of an inspection of the sensitive areas of the aircraft using the testing apparatus. This entails a relatively long testing period and the presence of a qualified operator, thereby leading to a relatively high maintenance cost.

As far as the designer of this device knows, there is currently no effective means for inspecting the status of structures, e.g., aeronautical structures, throughout their periods of use, and in particular for carrying out an overall evaluation of the health of aeronautical structures while the airplane is in flight.

SUMMARY

The disclosed embodiments propose a device suited to such an inspection, which enables the structural health of a structure to be monitored throughout its use by local measurements of the vibratory behavior of said structure. The problems faced by such a device are:

- to provide a non-destructive means of testing suitable for easy attachment to the surface of the structures to be tested, whether or not they are accessible, while still being of negligible mass and size and requiring little electrical power to operate;
- to provide a means of testing suitable for permanent installation on the structures to be tested during their use, so as to conduct predictive maintenance by detecting the appearance of defects as soon as possible, thereby enabling work to be scheduled and repairs to be carried out more cheaply, and ensuring maximum structural safety;
- to provide a means of testing that enables automatic management of the inspections and that provides a full analysis of the structures' health, so as to reduce the operator's work as much as possible in order to reduce the cost of maintenance.

For this purpose, the disclosed embodiments present a non-destructive testing device for a structure liable to contain a defect. According to the disclosed embodiments, said device contains means for measuring the vibratory waves emitted by said structure at various points on the surface of said structure, said means of measuring being incorporated in a flexible housing capable of adhering to the surface of said structure being tested.

Said means for measuring vibratory waves consist of a set of microsensors capable of generating a map of the vibrations on the surface of the structure.

Usefully, the dimensions and layout of the microsensors are selected to be capable of detecting changes in vibrations caused by the presence of defects of the smallest size targeted for detection.

According to the disclosed embodiments, the means of detection are piezoelectric microsensors arranged in a matrix of lines and columns, said microsensors transforming said vibratory waves emitted by said structure into electrical signals.

According to an embodiment the device also contains an interface electronics assembly connecting said means of detection and measurement to a recording memory, said interface electronics and said memory also being incorporated into said flexible housing so as to usefully form a monolithic testing device.

To transform the vibratory waves emitted by the structure into electrical signals, each microsensor contains a system of piezoelectric strips arranged between two conductive plates, the ends of said strips being fixed to the plates by means of a conductive adhesive material, and one of the two plates being fixed to said flexible housing, said two plates being themselves connected to said interface electronics.

The testing device usefully contains a calculating system such as a microprocessor system to automatically identify the vibratory waves caused by a defect present in the structure, based on the vibratory waves measured by the microsensors.

In an embodiment in which the calculating system is not incorporated into the flexible housing and connected to the testing device, said testing device contains a means of transmitting, to send the electrical signals recorded in the memory to said calculating system by using a wireless radio or infrared link.

In another embodiment in which the calculating system is incorporated into the flexible housing and is connected between said interface and the recording memory. [fragment]

According to one embodiment of the calculating system, it includes a memory containing at least one reference map of the vibratory waves from the structure(s), a means of calculation for converting the electrical signals sent by the testing device into vibratory waves, and means for the differential and spectral analysis of said vibratory waves measured by the microsensors by comparison with the reference vibratory waves.

According to one specific embodiment, the means of differential analysis contain a means of generating a status signal S, characteristic of the fact that the differential value between the reference vibratory waves and the vibratory waves measured by the microsensors exceeds a threshold value.

According to another specific embodiment, the spectral-analysis devices contain a means of generating a status signal S', characteristic of the fact that the frequency representation of the vibratory waves measured by the microsensors compared with the frequency representation of the reference vibratory waves contains spectral lines corresponding to vibratory waves caused by the presence of a defect in said structure.

Usefully, according to the embodiments described above, the generated status signals S and S' are either transmitted by the calculating system to a means of alarm or recorded in the recording memory of the testing device, and then sent to the means of alarm by using a wireless radio or infrared link.

The means of alarm may contain a display panel and light and/or sound indicators. Usefully, the piezoelectric strips are designed to detect both low-frequency and high-frequency vibratory waves.

Usefully, the testing device contains a self-feeding system in which at least one line or one column of said microsensors is connected to an accumulator of electrical energy designed to store the electrical energy generated by said microsensors and to return said electrical energy in the form of a current, to supply the testing device.

Other characteristics and advantages of the disclosed embodiments will be better understood by reading the following description and referring to the drawings, which show:

During the normal operation of an aircraft, especially when in flight, the plane's various structures are excited by a number of energy sources, producing vibrations. For example, pressure waves from its motors excite the vibratory modes of the structures, whose responses are characteristic of said structures. When a structure is altered, for example by the appearance of a structural anomaly such as a crack or a disturbance in these structures, the vibratory response is changed. The corresponding vibrations are superimposed on the structural vibrations from the excitation sources. A temporal and spectral analysis of the vibratory waves enables the characteristics of the vibrations to be extracted, allowing detection of abnormal modes that may signal the appearance of defects. Two categories of signals characteristic of a vibrating structure are generally distinguished. Low-frequency vibratory waves, in the low-frequency band between 0 and about 25 kHz, which express macro-movements of the structure around a fixed position (macroscopic-scale deformation), and high-frequency waves, in the band from about 20 kHz to a few MHz, which express movements at the microscopic scale within the material constituting the structure (microscopic deformation).

An analysis of the low-frequency vibratory waves enables detection of the presence of defects of mechanical origin, while analysis of the high-frequency vibratory waves enables detection of the initiation of small-scale defects such as cracks, or even defects related to corrosion, which generally tend to grow, and enables the development of these defects to be monitored.

DETAILED DESCRIPTION OF THE DISCLOSED EMBODIMENTS

Figure 1:
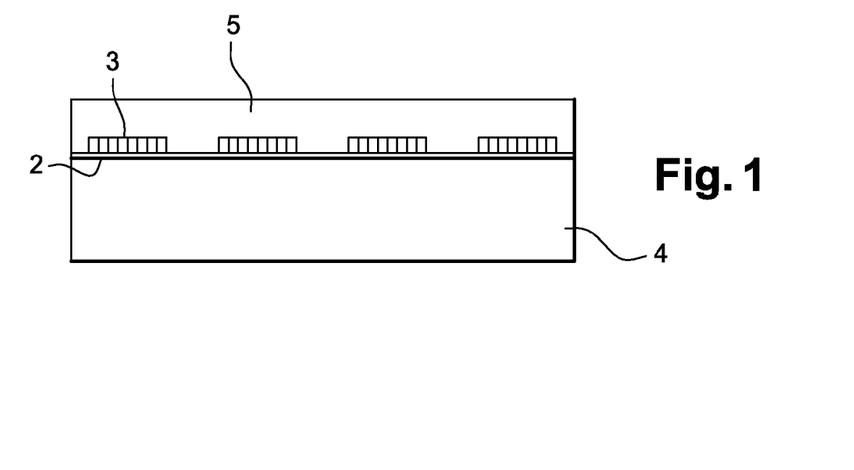
In FIG. 1: a schematic diagram of a side view of a section through a testing device containing a system of piezoelectric microsensors according to an embodiment, covering the surface of a structure to be tested, the testing device being itself covered by a coat of paint.

FIG. 1 shows a non-destructive testing device 1 on a structure 4 according to the disclosed embodiments, for detecting and measuring the vibratory waves caused by the presence of a defect in a structure.

It comprises a flexible housing 2 into which are incorporated the means of measuring 3 for vibratory waves emitted by said structure at various points on the surface of the structure. The flexible housing 2 may for example be made of a plastic material allowing the device to be attached to the surface of the structure to be tested, by following the shape of the structure.

The flexible housing of the testing device 1 is fixed to the surface of the structure 4 to be tested by means of an adhesive material.

This device should preferably be attached to a critical area of the structure where cracks are liable to appear. On an aircraft, the device may be placed on areas regarded as critical, located for example where the ailerons are coupled on, in areas where fuselage panels are joined together, and on important attachment components, e.g., those used for the motors.

Usefully, this testing device 1 is designed to receive a coating 5, which may for example be a coat of paint that covers testing device 1.

The means of measuring contain a system of piezoelectric microsensors 3, preferable arranged in a matrix of lines and columns. Each microsensor is capable of transforming the vibratory waves that it receives from the structure on which it is placed into electrical signals.

Figure 2:
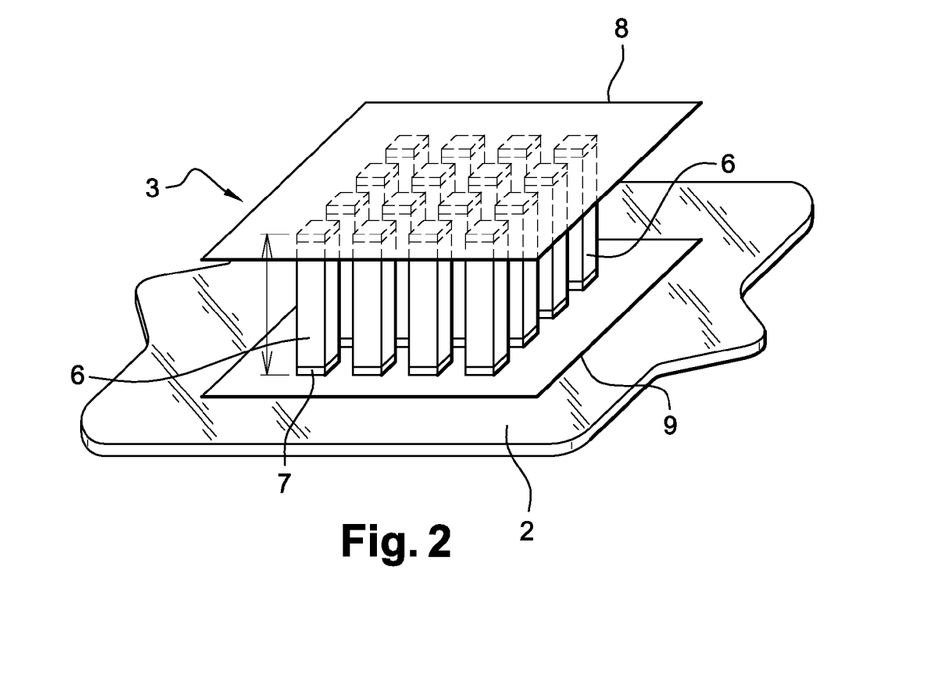
In FIG. 2: a schematic diagram of a partial section of a piezoelectric microsensor from FIG. 1, containing a system of piezoelectric strips arranged between two plates, the microsensor being incorporated into a flexible housing.

FIG. 2 diagrams a sectional view of one of the system's microsensors. It contains an assemblage of piezoelectric strips 6. Said assemblage of strips is placed between two conductive plates 8 and 9.

The ends of each strip are fixed onto the two conductive plates 8 and 9 by means of a conductive adhesive material 7, one of the two plates being fixed to the flexible housing 2, which is intended to cover the surface of an area of the structure being tested.

When the structure being tested vibrates, the piezoelectric strips vibrate at the same frequency as the point on the structure where the microsensor is placed. When deformed, the strips become electrically charged by the piezoelectric effect. The two conductive plates 8 and 9 connected to the ends of the strips collect the electrical signals generated by the electrical charges on the strips.

Figure 3:
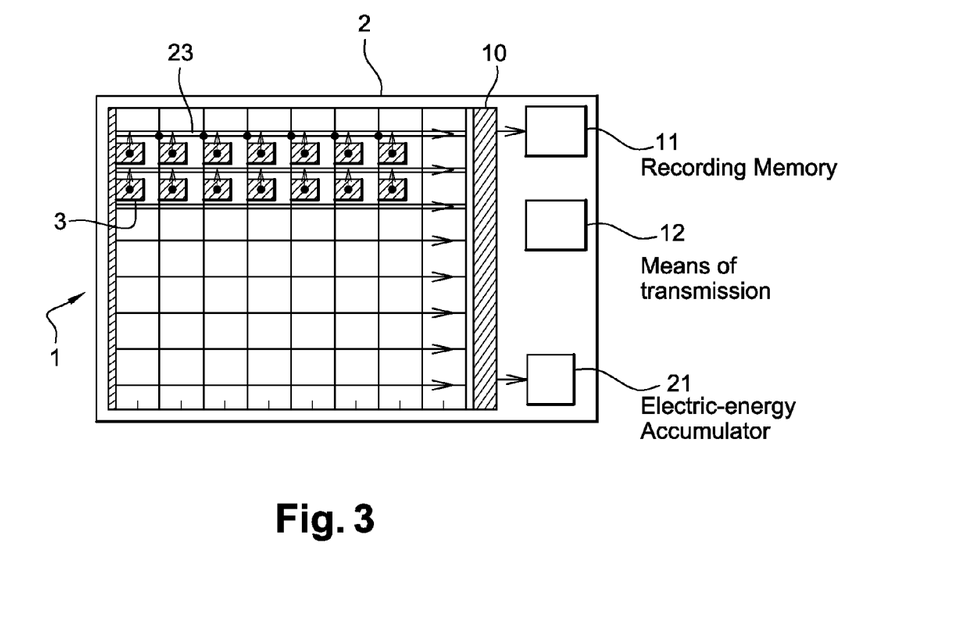
In FIG. 3: a schematic diagram of a top view of a testing device, showing an embodiment of the device.

FIG. 3 is a schematic diagram of a top view of the testing device, according to a specific embodiment; it has an approximately rectangular shape, here for example containing, by way of example, a system of 56 microsensors 3 arranged in a matrix of lines 3l and columns 3c. In addition, the device usefully contains an interface electronics assembly 10 connecting the microsensor system 3 to a recording memory 11. The electronics 10 and the memory 11 are preferably incorporated into the flexible housing 2 so as to usefully provide a monolithic testing device.

The electrical signals collected by the plates 8 and 9 from each microsensor are sent to the interface electronics 10, which should preferably contain a means for amplifying said electrical signals. The amplified signals are then sent to the recording memory 11. The interface electronics are placed at the end of the microsensor lines in the embodiment of the device shown in FIG. 3. In another embodiment, the interface electronics may be placed at the end of the microsensor columns, but other relationships between the microsensors and the interface electronics are possible under the disclosed embodiments.

Each microsensor 3 provides information on the structure's vibrations at the location of the microsensor, and the distribution of the microsensors enables a mapping of the vibratory waves on the surface of said structure, so that a defect in the structure that causes a local alteration in the vibratory waves can be located in relation to the microsensors.

In order to locate the defects precisely, the spacing between microsensors is set at a value less than the minimum size of the defects to be detected, such that the position of the defects can be determined, and such that in the event of local damage to the microsensor network the microsensors located around the damaged area will always allow monitoring of the areas that are close enough to a possible defect that the defect can be recognized and detected.

In a specific embodiment, the mode of transfer of the electrical signals coming from the microsensors 3 to the interface electronics 10 is an interline transfer mode. Above each line of microsensors there is a storage line 23. The signals are temporarily stored in this storage line 23. The content of the storage lines is then transferred to the interface electronics 10 in parallel mode. The electronic signals are then removed in series to a recording memory 11.

In a variant of the electrical-signal transfer mode, each microsensor is addressed directly to send its electric signals directly to the interface electronics 10.

Figure 4:
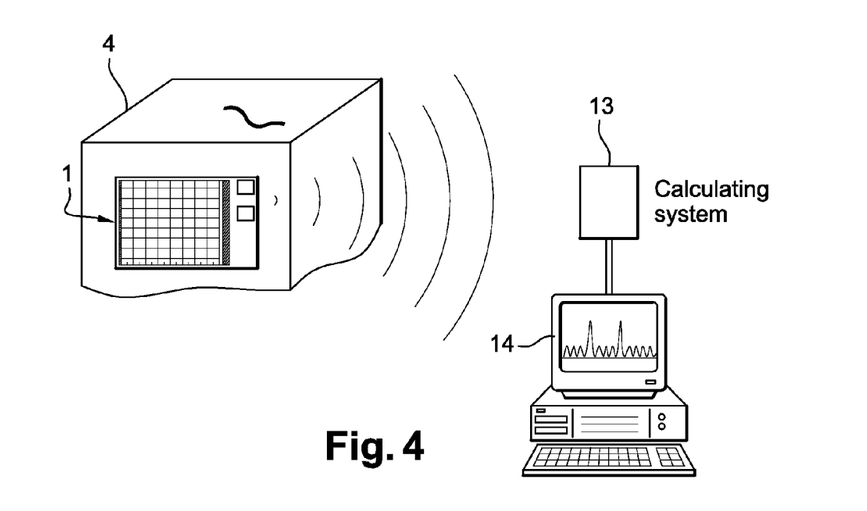
In FIG. 4: a schematic diagram of an embodiment of the testing device from FIG. 3 in operating position for transmitting electrical signals to a remote calculating system, In FIGS. 5A, 5B, and 5C: schematic diagrams of various stages in a practical example of UV photolithography used to obtain a system of strips.

In order to automatically process the electrical signals measured by the microsensors 3, the testing device also contains a calculating system 13, as shown diagrammatically in FIG. 4, to convert the electrical signals characteristic of the measured vibratory waves into digital values, and to identify the vibratory waves caused by the presence of a defect in the structure, by using the vibratory waves measured by the microsensors. The calculating system may be a microprocessor system.

In a preferred embodiment, shown in FIG. 4, since the calculating system is not incorporated into the flexible housing 2, the device contains a means of transmission, identified by the number 12 on FIG. 3, to send the electrical signals recorded in the recording memory 11 to the calculating system 13 by using a wireless radio or infrared link. This means of transmission contains for example a transponder integrated into the flexible support, which preferably operates on a fixed frequency, said frequency being chosen so that the transmission of the electrical signals representing the vibratory waves does not interfere with the transmission of other data by devices other than the testing device.

The calculating system should preferably contain an analog/digital converter to convert the analog electrical signals obtained from the recording memory into digital values. These digital values are then converted into vibratory waves by the means of calculation, which usefully incorporates a theoretical or experimental model defining the relationship between the vibration detected and the electrical charge generated.

To identify the variation in the vibrations caused by the presence of a defect in the structure, using the vibratory waves measured by the microsensors, the system contains a means of analysis to perform a comparative study of the amplitudes and frequencies of the vibratory waves measured by the microsensors versus those of the reference vibratory waves. For this purpose the calculating system contains a memory in which a database of reference vibratory-wave maps of the structure is recorded. The reference mapping constitutes a predefined model for comparison with the behavior of the area covered by the testing device. This mapping can be predetermined on a reference structure. "Reference structure" means a structure considered not to contain any defect, e.g., a structure leaving the end of its production line, having successfully completed all the qualification stages. It may also be predetermined by modeling. When the means of analysis perform an amplitude comparison between the reference vibratory waves and the vibratory waves measured by the microsensors, if the calculated differential value between the reference vibratory waves and the measured vibratory waves exceeds a threshold value, a status signal S is generated by the means of analysis.

This amplitude comparison is usefully supplemented by a spectral analysis. For example, the means of analysis first performs a Fourier transformation of the measured vibratory waves to obtain a frequency diagram of the vibration. By comparing the frequency diagram of the reference vibratory waves with the frequency diagram of the measured vibratory waves, the means of analysis then extracts spectral lines corresponding to the vibratory waves caused by the presence of a defect in the structure; this generates a second status signal S'.

Usefully, the spectral analysis enables identification of the nature of the defects encountered. A vibratory spectrum generally contains a set of lines. For easy identification of the lines corresponding to defects, and to classify them by type of defect encountered, a library of spectral configurations is preferably also recorded in the calculating system's memory.

The status signals S and S' as well as all information such as the nature of the defects, the size of the defects, and the locations of the defects are sent by the calculation system to the means of alarm 14 which may include a display panel to show the information and light and/or sound indicators 30 to warn the maintenance operator.

The transmission of electrical signals recorded in the memory 11 to the calculating system can be programmed so that it is carried out automatically, for example at the end of an aircraft's flight. This transmission can also be activated manually by the maintenance operator, by querying the testing device during inspection of the plane.

In another embodiment, the calculating system 13 is directly incorporated into the flexible housing 2 and connected between the interface electronics 10 and the recording memory 11. In this embodiment, the calculating system 13 receives the electrical signals directly from the interface electronics 10 and sends only the status signals S and S' and information on defects to the recording memory 11. During an inspection, by querying the device, the operator downloads the status signals and the information recorded in the testing device's memory to the means of alarm 14 by using a radio or infrared wireless link.

For real-time testing of the structures, the testing device may for example be programmed to be activated while the aircraft is no longer on the ground; it then performs measurements at regular intervals, e.g., every five minutes over a period selected so as to provide a time-based mapping. In this way the testing device enables a mapping of the area monitored over time, to define the development of the vibratory-wave field emitted by the part.

Figure 5A:
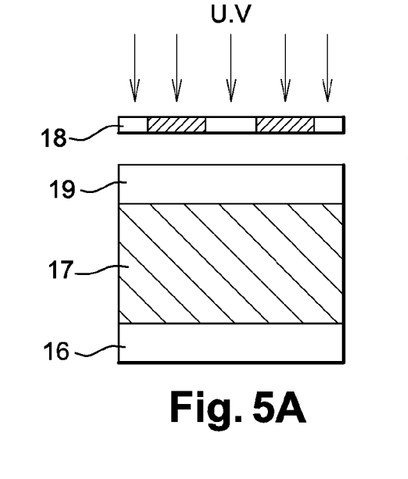
Figure 5B:
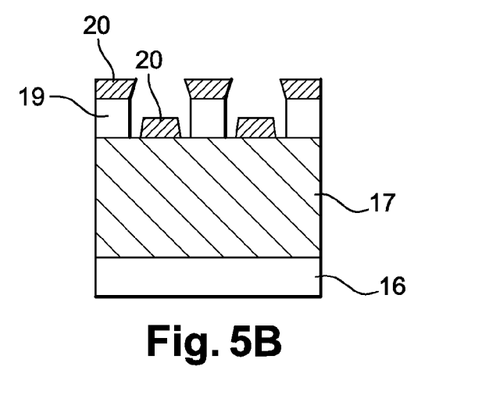
Figure 5C:
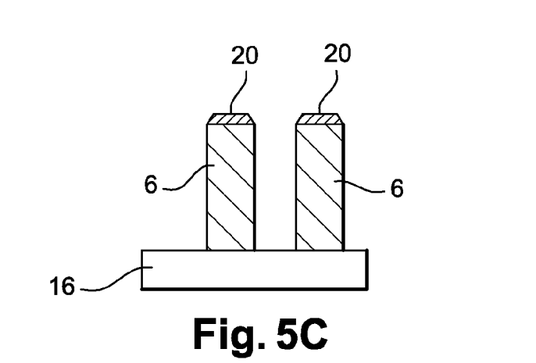

The strip system is produced by established techniques in the field of microelectronics. For example, the strip system may be obtained by the UV photolithography technique. FIGS. 5.A, 5.B, and 5.C show an example of the production of strips by the photolithographic technique. The piezoelectric film 17 is deposited on a hard substrate 16, of silicon or glass type; the thickness of the film 17 can be from several tens of nanometers to several tens of microns. A photosensitive film, for example resin 19, is deposited on the piezoelectric film and exposed to UV light through a mask 18. FIG. 5.B shows the assemblage after having been dipped in a developing solvent and subjected to metallization. The surface of the piezoelectric film 17 then contains metalized areas 20 deposited on the surface of the piezoelectric film and on the resin areas.

When removed in a bath of solvent the resin areas take with them the metal deposited on their surface, leaving on the surface of the piezoelectric film 17 the desired metallic patterns, which constitute a mask for the dry-etching stage. The deposited metal has a much lower rate of etching than that of the piezoelectric film 17, and by controlling the etching time and the speed of etching a system of regularly-spaced strips is produced by carrying out the etching through the mask of metal. The width of the strips can be from several tens of nanometers to several micrometers, and the interval between strips can be from several tens of nanometers to several micrometers.

Figure 6:
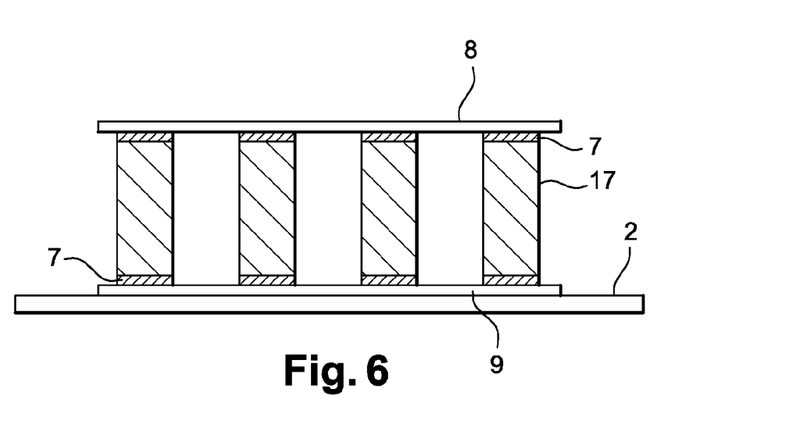
In FIG. 6: a schematic diagram of a side view of a section of a system of strips incorporated into a flexible housing.

In order to place the strip system thus obtained between two conductive plates 8 and 9, and then incorporate it into a flexible housing 2 to create the microsensors 3, we first take a conductive plate 8, which is fixed to the strip system by means of a conductive adhesive material 7. The hard substrate 16 can then be removed by ablation with a laser. The strip system is then fixed onto a second plate 9 by using a conductive adhesive material 7. The final stage consists of fixing the assembly onto the flexible housing 2, using an adhesive.

FIG. 6 shows a side view of a section of a system of piezoelectric strips 17 sandwiched between the two conductive plates 8 and 9 thus obtained. The microsensors thereby produced are then arranged at regular intervals to form a network of microsensors, as shown for example in FIG. 3. The material used to produce the piezoelectric strips may for example be a piezoelectric film 17 of lead zircotitanate (PZT) type. The piezoelectric strips 6 are preferably made from materials having a high piezoelectric coefficient and a sufficiently high Curie temperature (the temperature above which the material loses its piezoelectricity) to function in the temperature range encountered by the device in operational use. The piezoelectric strips are designed to receive both the low-frequency vibratory waves caused by macro-movements of the structure around a fixed position, and also the high-frequency waves caused by internal micro-movements of the material.

All the other electronic components incorporated in the flexible housing are produced by a micro-manufacturing technology on a hard substrate such as silicon or glass, transposed here on a plastic substrate. The temperature used during the micro-manufacturing process is liable to destroy the plastic substrate, and thus does not allow the components to be directly produced on a flexible substrate. To address this technical problem, one of the options currently proposed is to produce the components first on a hard substrate, itself deposited on glass. Another layer of glass to serve as protection is then fixed onto the components with a soluble adhesive, and the hard substrate is then removed from the stack by ablation with a laser. The components are then applied to a plastic substrate and fixed to it with a permanent adhesive, and the protective glass is removed.

According to a specific embodiment of the device, the testing device has a thickness of no more than 50 µm, and an area of about 10×10 cm on a side. The size of each microsensor is about one hundred microns and the space between two microsensors is about ten microns.

Figure 7:
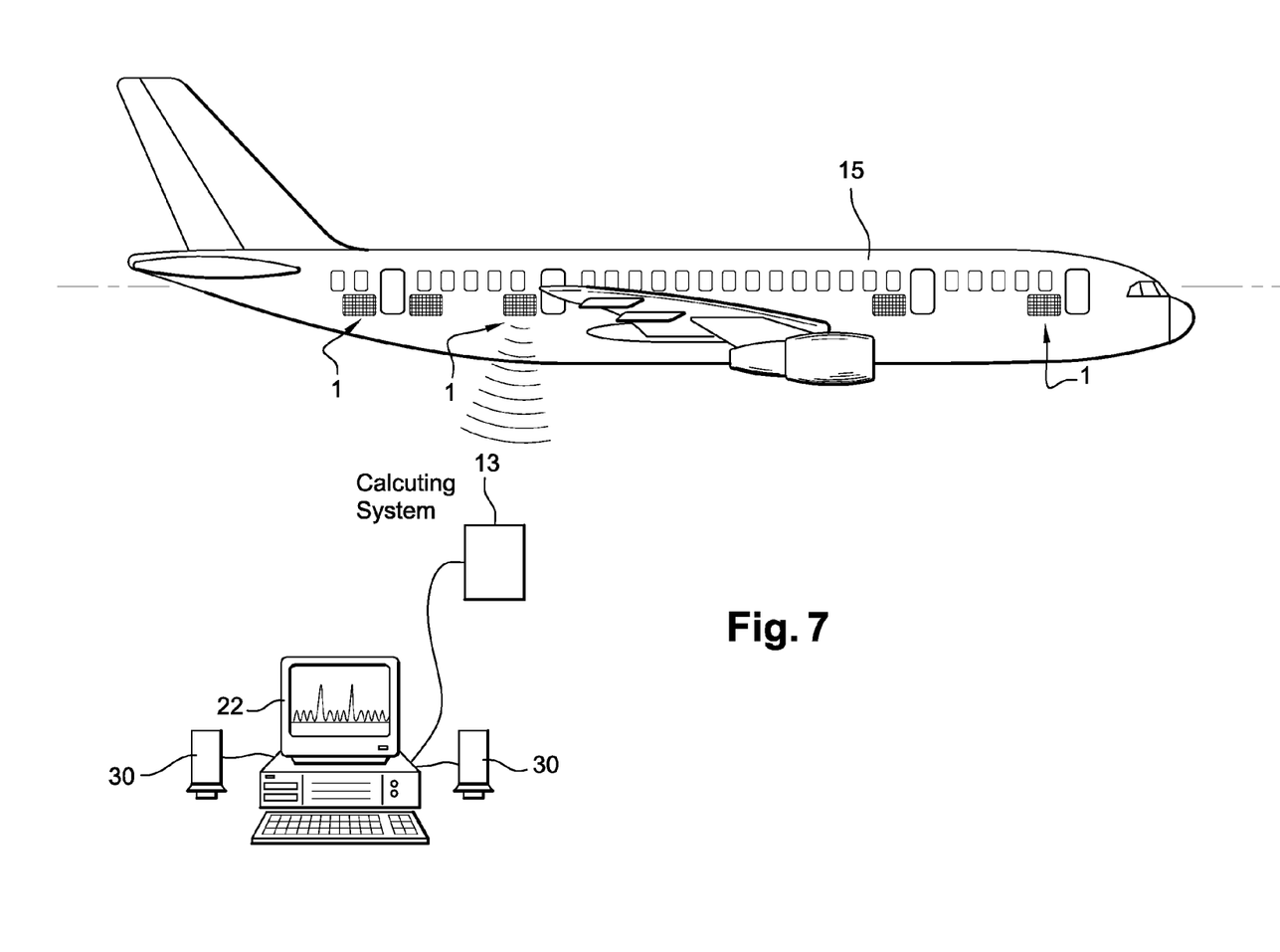
In FIG. 7: a schematic diagram of a network of testing devices arranged on the surface of the structures of an airplane on the ground, in position to transmit the signals recorded while the plane was in flight.

FIG. 7 is a schematic view comprising a network of several testing devices according to the invention, arranged on the surfaces of the structures of an aircraft 15. The plane is on the ground and the network of testing devices is transmitting the signals recorded during one or more flights by the aircraft to a calculating system 13, which is connected to a means of alarm 14; here, these include a computer with a monitor and sound indicators 30.

Usefully, the device contains a self-feeding system for the piezoelectric microsensors, for example at least one line or column of microsensors in the device is connected to an electric-energy accumulator 21 designed to store the electric energy generated by at least one line or at least one column of microsensors under the effect of the structure's vibrations. This accumulator returns the electric energy in the form of a current to supply the testing device.

The disclosed embodiments are put forward for testing aircraft structures, but can be used whenever a structure subjected to vibratory excitation sources must be monitored to detect the presence of a defect, e.g., in other industrial sectors such as the automotive, railroad, naval-construction, or nuclear sectors.

The invention claimed is:

1. A non-destructive testing device for a structure liable to contain a defect, said device containing interface electronics connecting a set of piezoelectric microsensors to a recording memory, said set of piezoelectric microsensors, said interface electronics and said recording memory being incorporated into a flexible housing capable of adhering to a surface of said structure to be tested, said set of piezoelectric microsensors being arranged in a matrix of lines and columns for:
    measuring vibratory waves emitted by said structure at various points on the surface of said structure, and
    transforming said vibratory waves into electric signals, wherein said interface electronics are placed at an end of the microsensors lines or at an end of the microsensors columns in order to connect respectively each line or each column of said set of piezoelectric microsensors to said interface electronics.

2. A device according to claim 1, wherein said set of microsensors is capable of generating a map of the vibratory waves on the surface of the structure.

3. A device according to claim 1, wherein the size of each microsensor is about one hundred microns and the space between two microsensors is about ten microns.

4. A testing device according to claim 1, wherein said interface electronics and said recording memory are incorporated into said flexible housing so as to form a monolithic testing device.

5. A testing device according to claim 1, wherein each microsensor contains a set of piezoelectric strips placed between two conductive plates electrically charged by the piezoelectric effect, the ends of said strips being fixed to said plates by means of a conductive adhesive material, one of the two plates being fixed to said flexible housing, said two plates being connected to said interface electronics to send electrical signals generated by the electrical charges on said strips to said interface electronics.

6. A testing device according to claim 5, wherein said piezoelectric strips are capable of detecting low-frequency vibratory waves in a frequency band of from 0 to about 25 kHz.

7. A testing device according to claim 5, wherein said piezoelectric strips are capable of detecting high-frequency vibratory waves in a frequency band of from about 25 kHz to a few MHz.

8. A testing device according to claim 5, wherein said piezoelectric strips are spaced at regular intervals.

9. A testing device according to claim 1, wherein said testing device contains a calculating system to automatically identify variations in the vibratory waves caused by the presence of a defect in the structure, based on the vibratory waves measured by said microsensors.

10. A testing device according to claim 9, wherein said calculating system not being incorporated into the flexible housing, said testing device contains a means of transmission for sending the electrical signals representative of the vibratory waves recorded in the memory to said calculating system by using a radio or infrared wireless link.

11. A testing device according to claim 9, wherein said calculating system is incorporated into said flexible housing and is connected between said interface electronics and said recording memory.

12. A testing device according to claim 9, wherein the calculating system includes a memory containing at least one map of reference vibratory waves for the structure, a means of calculation for converting the electrical signals generated by the microsensors into calculated vibratory waves, and means for the differential and spectral analysis of said calculated vibratory waves by comparison to the reference vibratory waves.

13. A testing device according to claim 12, wherein the means of differential analysis contain a means of generating a status signal S characteristic of the fact that a value for the differential between the reference vibratory waves and the calculated vibratory waves exceeds a threshold value.

14. A testing device according to claim 13, wherein the means of spectral analysis contain a means of generating a status signal S' characteristic of the fact that the frequency display of the calculated vibratory waves, compared with the frequency display of the reference vibratory waves, contains spectral lines corresponding to abnormal vibratory waves caused by the presence of a defect in said structure.

15. A testing device according to claim 14, wherein said status signals S and S' are sent by said calculating system to a means of alarm.

16. A testing device according to claim 15, wherein said generated status signals are recorded in said recording memory connected to said calculating system, and then retransmitted to the means of alarm by using a radio or infrared wireless link.

17. A testing device according to claim 15, wherein said means of alarm include a means of display and light or sound indicators.

18. A testing device according to claim 1, wherein the thickness of said testing device is no greater than 50 μm.

19. A testing device according to claim 1, wherein said device contains a self-feeding system in which at least one line or one column of said microsensors is connected to an accumulator of electric energy designed to store electric energy generated by said one or more microsensor lines or columns of microsensors and to return said electric energy in the form of a current to supply the testing device.

20. A testing device according to claim 1, wherein said flexible housing of the testing device is fixed to the surface of the structure to be tested, by means of an adhesive material.

* * * * *